(12) United States Patent
Higgins et al.

(10) Patent No.: US 11,499,707 B2
(45) Date of Patent: Nov. 15, 2022

(54) LIGHT FIXTURE HAVING A FAN AND ULTRAVIOLET STERILIZATION FUNCTIONALITY

(71) Applicant: Calyx Cultivation Tech. Corp., Houston, TX (US)

(72) Inventors: John C. Higgins, Houston, TX (US); Mark Sam, Bellaire, TX (US)

(73) Assignee: CalyxPure, Inc., Houston, TX (US)

( * ) Notice: Subject to any disclaimer, the term of this patent is extended or adjusted under 35 U.S.C. 154(b) by 4 days.

(21) Appl. No.: 16/846,816

(22) Filed: Apr. 13, 2020

(65) Prior Publication Data
US 2021/0317981 A1    Oct. 14, 2021

(51) Int. Cl.
| | | |
|---|---|---|
| *F21V 33/00* | (2006.01) | |
| *F21V 29/70* | (2015.01) | |
| *A61L 9/20* | (2006.01) | |
| *F21V 3/00* | (2015.01) | |
| *F21V 23/00* | (2015.01) | |
| *F21Y 115/10* | (2016.01) | |

(52) U.S. Cl.
CPC ............ *F21V 33/0064* (2013.01); *A61L 9/20* (2013.01); *F21V 3/00* (2013.01); *F21V 23/003* (2013.01); *F21V 29/70* (2015.01); *A61L 2209/12* (2013.01); *A61L 2209/14* (2013.01); *F21Y 2115/10* (2016.08)

(58) Field of Classification Search
None
See application file for complete search history.

(56) References Cited

U.S. PATENT DOCUMENTS

| | | | |
|---|---|---|---|
| 3,670,193 | A | 6/1972 | Thorington et al. |
| 3,992,646 | A | 11/1976 | Corth |
| 5,012,609 | A | 5/1991 | Ignatius et al. |
| 5,278,432 | A | 1/1994 | Ignatius et al. |
| 6,242,752 | B1 | 6/2001 | Soma et al. |

(Continued)

FOREIGN PATENT DOCUMENTS

| | | |
|---|---|---|
| CA | 2856725 | 6/2013 |
| CN | 201797809 | 4/2011 |

(Continued)

OTHER PUBLICATIONS

Argyroudi-Akoyunoglou et al., "Photoinduced Changes in the Chlorophyll a to Chlorophyll b Ratio in Young Bean Plants," Plant Physiology, Aug. 1970, 46(2), pp. 247-249.

(Continued)

*Primary Examiner* — Andrew Smyth
(74) *Attorney, Agent, or Firm* — Lewis & Reese, PLLC

(57) ABSTRACT

A lighting fixture is disclosed with effective disinfection properties against bacteria, fungi, and viruses. The fixture includes a fan to continuously draw air into the light fixture. The air drawn in is irradiated with UV radiation within the fixture, such as is provided from UV LED chips. The relatively small volume of the light fixture allows the flux or energy density of the UV radiation to be made more intense. After the air is sterilized, it can be put back into the room or building in which the fixture is placed. The white light provided by white light LEDs in the fixture provides illumination, and can further provide significant emission peaks at 405 nm and 470 nm which is also useful to pathogen inactivation.

19 Claims, 8 Drawing Sheets

(56) References Cited

U.S. PATENT DOCUMENTS

| | | |
|---|---|---|
| 6,791,259 B1 | 9/2004 | Stokes et al. |
| 7,658,891 B1 | 2/2010 | Barnes |
| 8,074,397 B2 | 12/2011 | Yoneda |
| 8,297,782 B2 | 10/2012 | Bafetti |
| 8,302,346 B2 | 11/2012 | Hunt et al. |
| 8,398,264 B2 | 3/2013 | Anderson |
| 8,453,376 B2 | 6/2013 | Chen |
| 8,476,844 B2 | 7/2013 | Hancock et al. |
| 8,508,204 B2 | 8/2013 | Deurenbeg et al. |
| 9,039,966 B2 | 5/2015 | Anderson et al. |
| 9,046,227 B2 | 6/2015 | Aurelien |
| 9,145,590 B2 | 9/2015 | Evans et al. |
| 9,162,077 B2 | 10/2015 | Nigola et al. |
| 9,333,274 B2 | 5/2016 | Peterson |
| 9,368,695 B2 | 6/2016 | Aurelien |
| 9,439,989 B2 | 9/2016 | Lalicki |
| 9,581,310 B2 | 2/2017 | Wu et al. |
| 9,681,515 B2 | 6/2017 | Rantala |
| 9,750,105 B2 | 8/2017 | Rantala |
| 10,104,740 B2 | 10/2018 | Rantala |
| 10,398,000 B2 | 8/2019 | Rantala |
| 10,440,900 B1 | 10/2019 | Higgins |
| 2003/0124023 A1 | 7/2003 | Burgess et al. |
| 2004/0008523 A1 | 1/2004 | Butler |
| 2005/0055070 A1 | 3/2005 | Jones et al. |
| 2005/0207159 A1 | 9/2005 | Maxik |
| 2006/0022582 A1 | 2/2006 | Radkov |
| 2006/0071589 A1 | 4/2006 | Radkov |
| 2006/0186377 A1 | 8/2006 | Takahashi et al. |
| 2006/0261742 A1 | 11/2006 | Ng et al. |
| 2006/0262545 A1 | 11/2006 | Piepgras et al. |
| 2006/0284199 A1 | 12/2006 | Matheson |
| 2008/0008620 A1 | 1/2008 | Alexiadis |
| 2008/0245788 A1 | 10/2008 | Choong et al. |
| 2008/0278927 A1 | 11/2008 | Li et al. |
| 2008/0305004 A1 | 12/2008 | Anderson et al. |
| 2008/0315217 A1 | 12/2008 | Van Der Wel |
| 2009/0018621 A1 | 1/2009 | Vogler et al. |
| 2009/0034236 A1 | 2/2009 | Reuben |
| 2009/0231832 A1 | 9/2009 | Zukauskas et al. |
| 2009/0267484 A1 | 10/2009 | Kasakura et al. |
| 2010/0001648 A1 | 1/2010 | De Clercq et al. |
| 2010/0121420 A1 | 5/2010 | Fiset et al. |
| 2010/0232135 A1 | 9/2010 | Munehiro et al. |
| 2010/0244724 A1 | 9/2010 | Jacobs et al. |
| 2010/0246169 A1 | 9/2010 | Anderson et al. |
| 2011/0315956 A1* | 12/2011 | Tischler .......... H05B 45/12 257/E33.048 |
| 2012/0068615 A1 | 3/2012 | Duong et al. |
| 2012/0099303 A1 | 4/2012 | Li et al. |
| 2012/0281408 A1 | 11/2012 | Owen et al. |
| 2012/0286304 A1 | 11/2012 | LeToquin et al. |
| 2012/0320607 A1 | 12/2012 | Kinomoto et al. |
| 2013/0077299 A1 | 3/2013 | Hussell et al. |
| 2013/0139437 A1 | 6/2013 | Maxik |
| 2013/0194795 A1 | 8/2013 | Onaka |
| 2013/0313516 A1 | 11/2013 | David et al. |
| 2013/0313546 A1 | 11/2013 | Yu |
| 2013/0318869 A1 | 12/2013 | Aikala |
| 2013/0320299 A1 | 12/2013 | Li |
| 2014/0034991 A1 | 2/2014 | McKenzie et al. |
| 2014/0152194 A1 | 6/2014 | Beyer |
| 2014/0254131 A1 | 9/2014 | Osinski et al. |
| 2014/0328046 A1 | 11/2014 | Aanegola et al. |
| 2015/0014715 A1 | 1/2015 | Hsing Chen et al. |
| 2015/0049459 A1 | 2/2015 | Peeters et al. |
| 2015/0083221 A1 | 3/2015 | Boonekamp et al. |
| 2015/0129781 A1 | 5/2015 | Kretschmann |
| 2015/0182646 A1 | 7/2015 | Anderson et al. |
| 2015/0196002 A1 | 7/2015 | Friesth |
| 2015/0342125 A1 | 12/2015 | Krijn et al. |
| 2016/0015840 A1 | 1/2016 | Gordon |
| 2016/0030610 A1* | 2/2016 | Peterson .......... A61L 2/084 362/84 |
| 2016/0088802 A1 | 3/2016 | Nicole et al. |
| 2016/0249810 A1 | 9/2016 | Darty et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2018/0147417 A1* | 5/2018 | Rantala .......... H01L 33/08 |
| 2018/0224093 A1 | 8/2018 | Dutta et al. |
| 2019/0113219 A1* | 4/2019 | Niemiec .......... A01M 1/08 |
| 2019/0292315 A1* | 9/2019 | Niemiec .......... C08G 81/00 |
| 2020/0009286 A1* | 1/2020 | Zarcone .......... F21S 9/022 |
| 2020/0288646 A1* | 9/2020 | Howe .......... A01G 7/045 |

FOREIGN PATENT DOCUMENTS

| | | |
|---|---|---|
| CN | 103947469 | 7/2014 |
| CN | 103947470 | 7/2014 |
| CN | 104056289 | 9/2014 |
| EP | 2554583 | 2/2013 |
| JP | S6420034 | 1/1989 |
| JP | 2003339845 | 12/2003 |
| KR | 1020130125436 A1 | 11/2013 |
| KR | 1020170114678 A | 10/2017 |
| KR | 102042655 B1 | 11/2019 |
| WO | 2001/014012 | 3/2001 |
| WO | 2002/067660 | 9/2002 |
| WO | 2003/063902 | 8/2003 |
| WO | 2004/033028 | 4/2004 |
| WO | 2006/100303 | 9/2006 |
| WO | 2006/126482 | 11/2006 |
| WO | 2007/012875 | 2/2007 |
| WO | 2007/049180 | 5/2007 |
| WO | 2009/045107 | 4/2009 |
| WO | 2009/056838 | 5/2009 |
| WO | 2013/141824 | 9/2013 |
| WO | 2014/188303 | 11/2014 |
| WO | 2015/066099 | 5/2015 |
| WO | 2016/019029 | 2/2016 |
| WO | WO-2018221505 A1 * | 12/2018 .......... E06B 5/00 |

OTHER PUBLICATIONS

Beelmann et al., "Post-harvest Vitamin D Enrichment of Fresh Mushrooms," HAL Project # MU07018, Apr. 30, 2009, Penn State University.

Carvalho et al., "Sequential Light Programs Shape Kale (*Brassica napus*) Sprout Appearance and Alter Metabolic and Nutrient Content," Horticulture Research 1, Article No. 8, 2014.

Eytan et al., "Changes in Photosystem I Activity and Membrane Organization During Degreening and Greening of a Chlamydomonas Reinhardi Mutant, y-1," The Journal of Biological Chemistry, vol. 249, No. 3, Issue of Feb. 10, , p. 738-744, 1974.

Kleuter et al., "Photosynthesis in Cucumbers with Pulsed or Continuous Light," Transactions of the ASABE, 23(2): 0437-0442, 1980.

Lefsrud et al., "Irradiance from Distinct Wavelength Light-Emitting Diodes Affect Secondary Metabolites in Kale," HortScience, vol. 43, No. 7, pp. 2243-2244, 2008.

Nicklisch, Andreas, "Growth and Light Absorption of Some Planktonic Cyanobacteria, Diatoms and Chlorophyceae Under Stimulated Natural Light Fluctuations," Journal of Plankton Research, vol. 20, Issue 1, pp. 105-119, 1998.

Olle et al., "The Effects of Light-Emitting Diode Lighting on Greenhouse Plant Growth and Quality," Agricultural and Food Science, vol. 22, No. 2, pp. 223-234, 2013.

Sforza et al., "Adjusted Light and Dark Cycles Can Optimize Photosynthetic Efficiency in Algae Growing in Photobioreactors," PLos ONE, 7(6): e38975, 2012.

Tennessen et al. "Efficiency of Photosynthesis in Continuous and Pulsed Light Emitting Diode Irradiation," Photosynthesis Research, 44(3), pp. 261-269, 1995.

Vänninen et al. "Prospecting the Use of Artificial Lighting for Integrated Pest Management," ISHS Acta Horticulturae, 956, pp. 593-608, 2010.

(56) References Cited

OTHER PUBLICATIONS

Yeh et al., "High-Brightness LEDs—Energy Efficient Lighting Sources and their Potential in Indoor Plant Cultivation," Renewable and Sustainable Energy Reviews, vol. 13, Issue 8, pp. 2175-2180, 2009.

R.M. Tomb et al., "New Proof-of-Concept in Viral Inactivation: Virucidal Efficacy of 405 nm Light Against Feline Calicivirus as a Model for Norovirus Decontamination," Food & Environmental Virology, vol. 9(2), 23 pages (2017).

A.J. DeLucca et al., "Blue Light (470 nm) Effectively Inhibits Bacterial and Fungal Growth," Letters in Applied Biology, vol. 55., pp. 460-466 (2012).

C.D. Ltyle et al., "Predicted Inactivation of Viruses of Relevance to Biodefense by Solar Radiation," J. Virology (vol. 79 (22), pp. 14244-14252 (2005).

K. Bergmann, "UV-C Irradiation: A New Viral Inactivation Method for Biopharmaceuticals," America Pharmaceutical Review, vol. 17(6) (Nov. 2014).

Pinter, Matt, et al., "IEC/EN 62471 (Eye Safety) for LED Lighting Products—Standards for Eye and Skin Safety," Smart Vision Lights, 2009, 4 pages.

Neumark, et al., "Wide Bandgap Light Emitting Materials and Devices," John Wiley & Sons, 2008, 50 pages.

Dai, Tianhong, et al., "Blue Light for Infectious Diseases: Propionibacterimn Acnes, Helicobacter Pylori, and Beyond?" National Institutes of Health—Drug Resist Update, Aug. 2012, 15(4), pp. 223-236.

Daicho, Hisayoshi, et al., "A Novel Phosphor for Glareless White Light-Emitting Diodes," Nature Communications, 3:1132, Oct. 16, 2012, 8 pages.

Setlur, Anant A., "Phosphors for LED-based Solid-State Lighting," The Electrochemical Society Interface, Winter 2009, 5 pages.

TRI-R Project Brochure, Toshiba Materials Co., LTD., retrieved on Aug. 18, 2017, 16 pages.

Extended European Search Report regarding corresponding EP Application No. 20201893.3, dated Mar. 30, 2021.

Communication Pursuant to Article 94(3) EPC regarding corresponding European Patent Application No. 20201893.3, dated Jan. 27, 2022.

\* cited by examiner

LIGHT FIXTURE HAVING A FAN AND ULTRAVIOLET STERILIZATION FUNCTIONALITY

FIELD OF THE INVENTION

This application relates to a lighting fixture having the ability to sterilize pathogens such as bacteria, fungi, and viruses.

INTRODUCTION

Lighting fixtures are common in commercial buildings and homes. For example, fluorescent bulb fixtures have been used in commercial buildings and homes for years. Over the last decade or so, Light Emitting Diode (LED) based lighting fixtures have been developed which generally have the same size, shape, and mounting hardware as do traditional fluorescent bulb fixtures (typically 2×2 feet or 2×4 feet). This allows older fluorescent bulb fixtures to be easily replaced by LED based fixtures, which is beneficial because LED fixtures are more energy efficient, more reliable, and easier to maintain when compared with fluorescent fixtures. Another benefit of LED fixtures is that they can provide radiation suitable to provide disinfection as well as providing visual white light. For example, U.S. Patent Application Publication 2018/0147417 discloses a LED chip useable in a lighting fixture. The LED chip includes a first LED that emits light at 405 nm in the near ultraviolet (UV) range. (The wavelength of light in the visible spectrum ranges from 380 nm at the UV end of the spectrum to 740 nm at the infrared (IR) end of the spectrum). The LED chip also includes a second LED that emits at 450 nm in the blue range of visible light. The LEDs in the chip are coated by a phosphor material, and for the most part the 405 nm radiation passes through the phosphor without absorption. The 450 nm radiation by contrast interacts with the phosphor where it is converted to higher wavelengths, which results in a broader white light emission spectrum. In sum, the LED chip produces an overall spectrum with a peak at 405 nm, as well as a broader-wavelength white spectrum. The inclusion of a significant amount of 405 nm light in the overall spectrum is beneficial, because radiation at that wavelength is known to disrupt certain microbial biological processes. For example, the '417 Publication explains that 405 nm radiation causes reactive oxygen species generation in cells, which in turn prevent cell metabolism and effectively suppresses bacterial growth. 405 nm radiation has also been reported as providing disinfection against fungi. See R. M. Tomb et al., "New Proof-of-Concept in Viral Inactivation: Virucidal Efficacy of 405 nm Light Against Feline Calicivirus as a Model for Norovirus Decontamination," Food & Environmental Virology, Vol. 9(2), pp. 159-67 (2017).

While LED fixture having disinfection properties such as those just described are beneficial, the inventor sees room for improvement. For one, other wavelengths—such as 470 nm—have also been shown to have antibacterial as well as antifungal properties. See, e.g., A. J. DeLucca et al., "Blue Light (470 nm) Effectively Inhibits Bacterial and Fungal Growth," Letters in Applied Biology, Vol 55, pp. 460-66 (2012). But wavelengths such as 405 nm and 470 nm may not be effective against viruses. The article by R. M. Tomb, cited above, investigates the use of 405 nm radiation to inactivate viruses, and while promising results were shown, it appears that much higher doses of 405 nm radiation may be necessary to provide viral disinfection. As 405 nm radiation may be irritating to human eyes, see '417 Publication, it may not be useful to increase the intensity of 405 nm radiation in an otherwise white-light LED fixture in the hopes that it will also kill viruses.

Furthermore, the flux or energy density of pathogen-inactivating radiation, such as at 405 and 470 nm, provided by a light fixture may not be sufficient to inactivate air borne pathogens. In short, the volume of the room in which a light fixture is placed may be too large to effectively inactivate air borne pathogens.

The inventor discloses a comprehensive solution in the form of a white light LED fixture with effective disinfection properties against bacteria, fungi, and viruses. As discussed further below, the white light LED fixture includes a fan to continuously draw air into the light fixture. The air drawn in is irradiated with UV radiation within the fixture, such as is provided from UV LED chips. The relatively small volume of the light fixture allows the flux or energy density of the UV radiation to be made more intense. After the air is sterilized, it can be put back into the room or building in which the fixture is placed. The white light provided by white light LEDs in the fixture provides illumination, and can further provide significant emission peaks at 405 nm and 470 nm which is also useful to pathogen inactivation.

DETAILED DESCRIPTION

Figure 1:
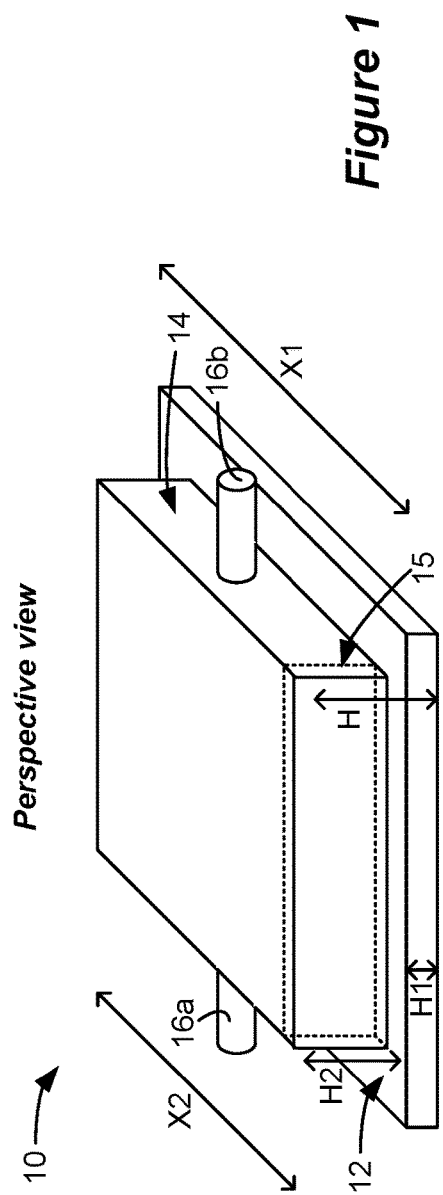
FIG. 1 shows various views of an improved lighting fixture, having a light box, a fan to draw in air, and a UV sterilization box through which the drawn air passes.
Figure 1:
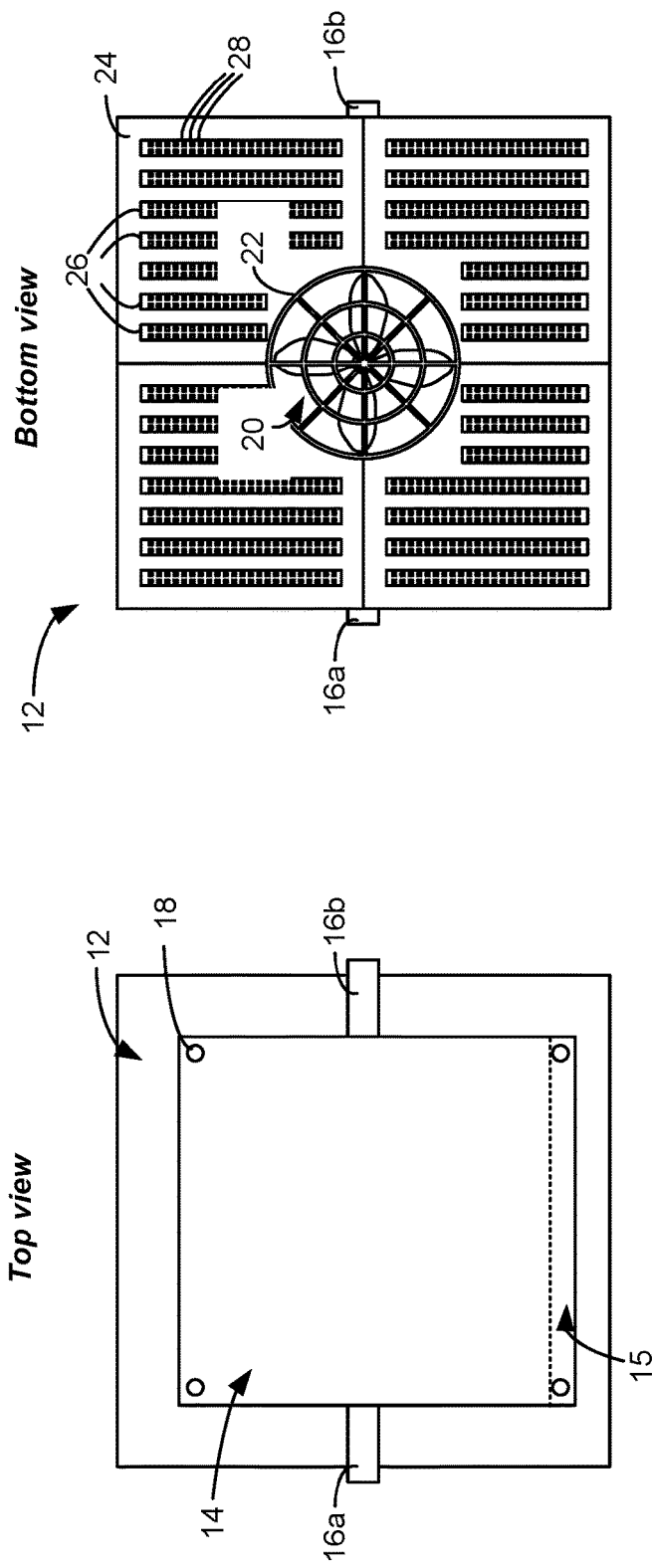

An example of a disinfecting light fixture 10 is shown in FIG. 1 in perspective, top down, and bottom up views. The fixture 10 has two main sections: a light box 12, and a UV sterilization box 14. Note that these "boxes" 12 and 14 do not need to be box-shaped as shown, and boxes 12 and 14 can instead be understood as any compartment, region, or volume in the fixture 10 however shaped and sized.

The light box 12 includes white LED chips 28 which provide for illumination and whose spectrum additionally and preferably includes significant radiation at 405 nm and 470 nm, as explained further below. The light box 12 includes a fan 20 protected by a grate 22. The fan 20 is used to draw air into the UV sterilization box 14 where the air is disinfected with UV radiation provided by UV LED chips 82 (FIG. 4), again discussed further below. One or more holes 66 (FIG. 3A) are present in the UV sterilization box 14, and hose connectors 16a and 16b can be fitted in these holes. The air drawn into the UV sterilization box 14 by the fan 20 exits the fixture 10 through these hose connectors 16a and 16, thus outputting sterilized air.

Notice then that the disinfecting light fixture 10 includes different means of providing sterilization of pathogens. The white LED chips 28, as well as providing white light for illumination, include significant radiation at 405 and 470 nm, which are useful in inactivating at least bacteria and fungi in the air and on surfaces in the room being illuminated, as discussed above. Other air borne pathogens—in particular viruses—are drawn into the fixture by the fan 20 and subjected to high intensity UV radiation provided by the UV LED chips 82 in the UV sterilization box 14. Such UV radiation should inactivate such air borne viruses, see C. D. Lytle et al., "Predicted Inactivation of Viruses of Relevance to Biodefense by Solar Radiation," J. Virology (Vol. 79 (22), pp. 14244-52 (2005), and would be expected to provide further sterilization of other air borne pathogens (bacteria and fungi) as well. The air as sterilized by the fixture 10 can then be put back into the room where the fixture 10 is located, or otherwise may be input into the air handling system of the building, as explained further below. Notice that the fixture 10's sterilization properties makes it particularly well suited for use in locations where pathogens can be problematic, such as hospitals, nursing homes, etc. Fixture 10 is also useful when incorporated into grow light systems use to grow plants, such as in the system described in U.S. Pat. No. 10,440,900, which is incorporated herein by reference in its entirety. Sterilization is important in this context as well, because growing plants are susceptible to pathogens such as viruses, bacteria, and fungi.

FIG. 1 shows an example of a 2×2 feet (X1) fixture 10, although the fixture could be made of any shape and size. The UV sterilization box 14 may be smaller in area, e.g., approximately 1.5×1.5 feet (X2). The total height H of the fixture 10 is preferably about six inches, with the light box 12 having a height of about 1.5 inches (H1) and the UV sterilization box 14 having a height of about 4.5 inches (H2). These dimensions are merely one example, and both the light box 12 and the UV sterilization box 14 can have other dimensions as well. The fixture 10 so sized comprises a suitable replacement for traditional fluorescent bulb fixtures. Means for mounting the fixture 10 (e.g., to a room's ceiling) are not shown, but can be of conventional design.

The top view shows that the UV sterilization box 14 can include a section 15 for necessary system electronics, as described later. The bottom view shows the underside of the fixture 10 that which would provide illumination into the room. The fixture 10's diffuser 40 (FIGS. 3A and 3B) is removed for easier viewing of underlying structures. Visible from this view are one or more circuit boards 24 which support LED strips 26. Each LED strip 26 includes a number of white LED chips 28, which are described in detail with respect to FIGS. 2A and 2B. The size, number, and location of the LED strips 26 is variable, as are the number, type, and location of the white LEDs chips 28 on these strips. In the example shown, there are four circuit boards 24, each being approximately 1×1 foot, although a single circuit board 24 could be used as well. Although not yet shown in the figures, the circuit board(s) include a hole 25 to accommodate the fan 20.

Figures 2A, 2B:
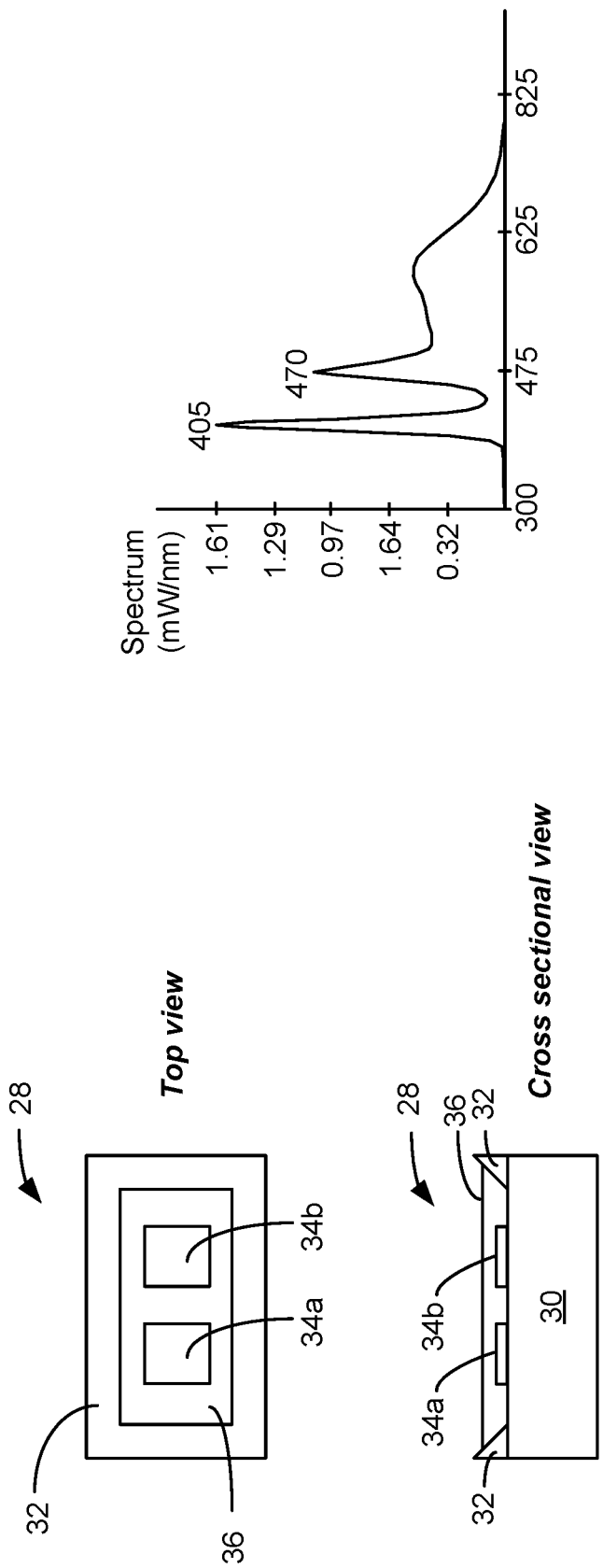
FIGS. 2A and 2B show white LED chips that can be used in the light box, which preferably produce a white light spectrum having significant near-UV peak wavelengths at 405 and 470 nm, which have shown to be useful to inactivate bacteria and fungi.

FIG. 2A shows an example of the white LED chip 28, while FIG. 2B shows the spectrum that results from use of this chip. A white LED chip 28 is shown in top down and cross sectional views, and includes two LEDs 34a and 34b mounted to a substrate 30. A cavity wall 32 surrounds the LEDs 34s and 34b and helps to direct light out of the chip 28. Preferably, the LEDs 34a and 34b are different, and emit at different peak wavelengths. For example, LED 34a can emit at a peak wavelength of 405 nm, while LED 34b can emit at a peak wavelength of 470 nm. In this example, the LEDs 34a and 34b are covered with a phosphor 36. The phosphor 36, as one skilled in the art will appreciate, can comprise a mixture of different photosensitive chemicals. Although electrical connections to the LEDs 34a and 34b within the chip 28 are not shown, the LEDs can be driven with a current in series or in parallel, or each can be independently driven by their own currents. Each of the LEDs 34a and 34b could also be covered with their own unique phosphors as well, or covered with no phosphor at all, although this isn't shown.

As shown in the emission spectrum of the white LED chip 28 in FIG. 2B, it is assumed that the 405 nm radiation largely breaks through the phosphor 36 without being absorbed, and thus this radiation does not substantially contribute to the production of longer wavelengths which would broaden the spectrum. Thus, the spectrum shows a sharp leak at 405 nm. The 470 nm radiation by contrast is designed to interact with the phosphor 36 to produce longer wavelengths, which broadens the spectrum from about 470 to 775 nm, which in sum produces white light useful for illumination. Some amount of the 470 nm radiation is not absorbed by the phosphor 36, and thus the spectrum includes another peak at this wavelength. Thus, the overall spectrum thus has significant high intensity peaks at 405 nm and 470 nm, but also a broad spectrum that in sum produces white light. In short, the white LED chips 28 in the light box 12 produce white light having significant intensities at 405 and 470 nm. As noted above, inclusion of these peak wavelengths is preferred in the disinfecting light fixture 10 because such radiation impedes (at least) bacterial and fungal growth. One skilled in the art will understand that the disinfection benefits provided by the LEDs 34a and 34b are still had even if the peak wavelengths produced by those LEDs are not exactly at 405 nm and 470 nm. In this regard, the LEDs 34a and 34b may produce radiation at approximately 405 nm and/or 470 nm, where approximately means a wavelengths that is plus or minus 10 nm from these ideal wavelengths—i.e., from 395 nm 415 nm (in the case of the 405 nm LED 34a), and from 460 nm to 480 nm (in the case of the 470 nm LED 34b).

Figure 3A:
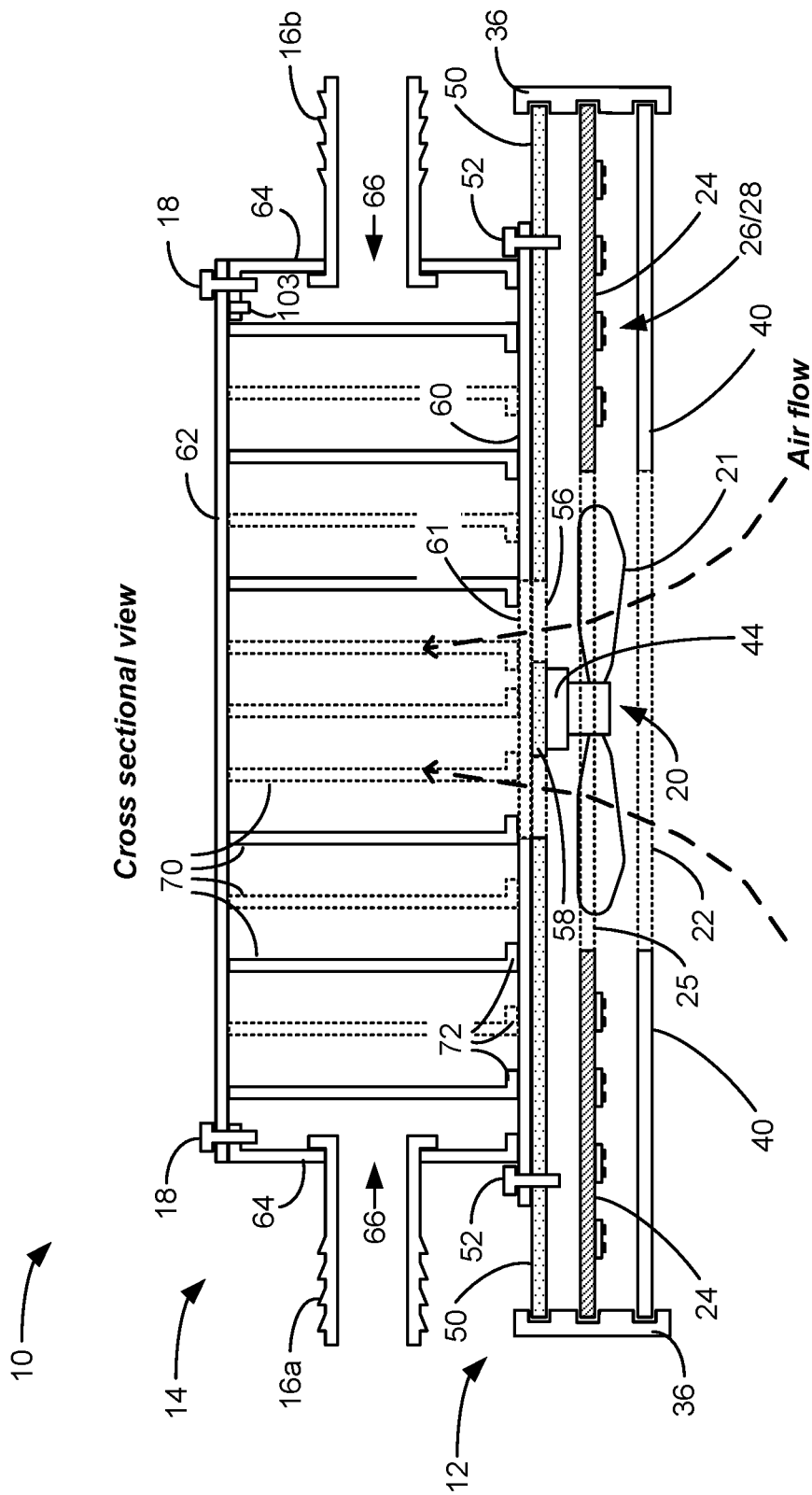
FIG. 3A shows a cross section of the lighting fixture.
Figure 3B:
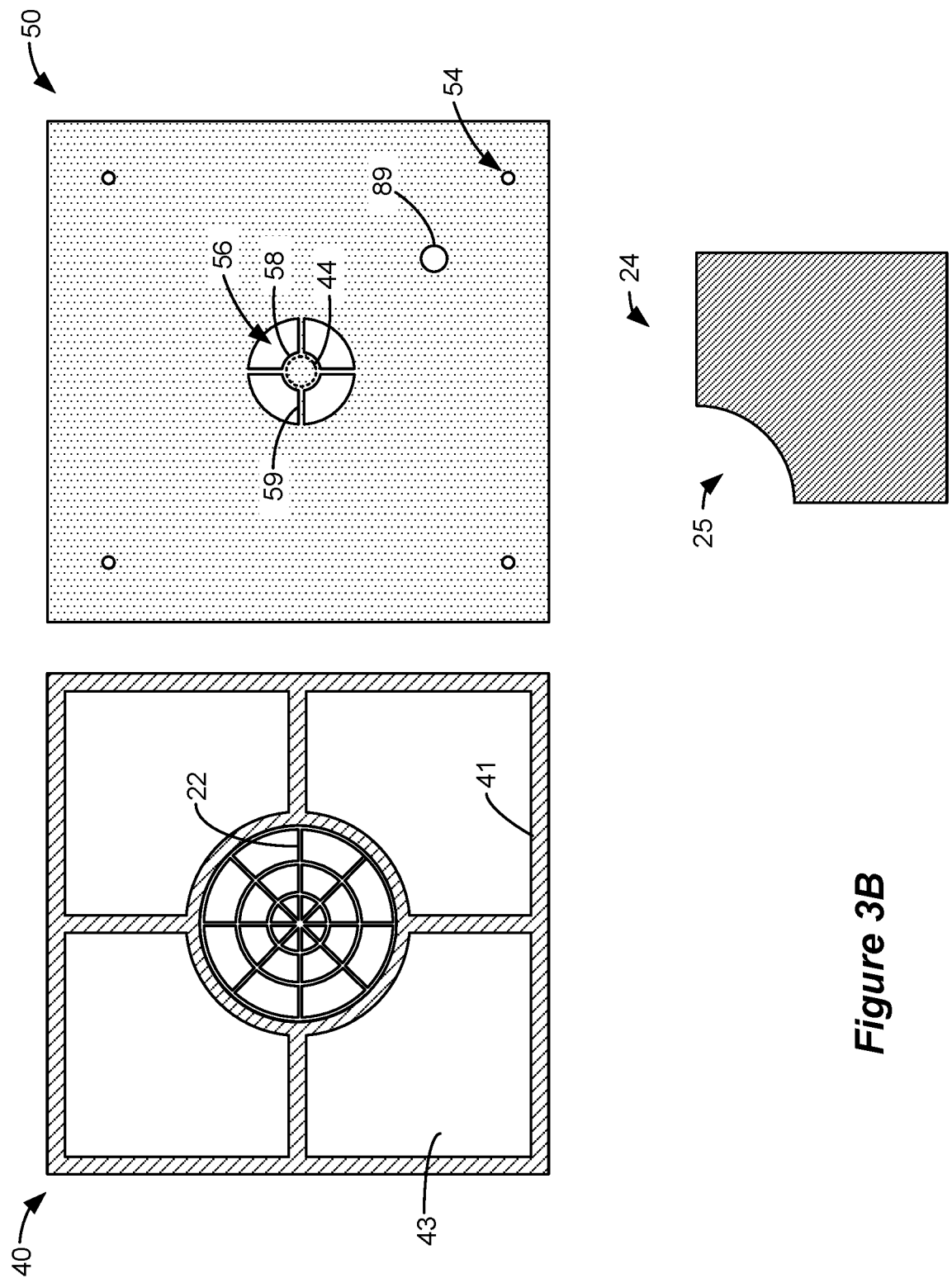
FIG. 3B shows the fixture's back plane, diffuser, and one of its circuit boards of the light box.

Further sterilization—in particular, of viruses—is provided by the UV sterilization box 14, although before discussing such details, the construction of the light fixture 10 is described, starting with FIGS. 3A and 3B. The light box 12 includes a diffuser 40, one or more circuit board sections 24 containing the LED strips 26 as already described, and a back plane 50. The diffuser 40, the circuit board(s) 24, and the back plane 50 are essentially formed in parallel planes inside the light box 12, and are held in place using a frame 36. This method of construction is described in U.S. Pat. No. 10,440,900, which was incorporated above. As explained in the '900 patent, the frame 36 can comprise four panels (for each of the four edges of the light box 12). These panels of frame 36 can be positioned around the diffuser 40, the circuit board(s) 24, and the back plane 50, and then connected to hold these structures securely in place.

The diffuser 40 is positioned between the white LED chips 28 and the room to be illuminated, and is shown in further detail in FIG. 3B. The diffuser 40 operates to scatter light produced by the white LED chips 28 to produce a combined emission spectrum (from white LED chips 28; FIGS. 2A and 2B) in the illuminated room that is more spatially homogenous. Preferably, the diffuser 40 includes a lens material 43 that is substantially transparent to the emission spectrum that the white LED chips 28 produce. The lens material 43 is typically made of various glass or plastic materials, such as a polycarbonate light-diffusing white material, and preferably allows good transmittivity of radiation at 405 and 470 nm in particular. The diffuser 40 can further include a brace 41, preferably made of a metallic material. The brace 41 acts to hold the lens material 43 and the fan grate 22, as well as providing a decorative element to the fixture 10. As shown, in this example, the brace 41 divides the diffuser 40 into quarters, and thus the lens material 43 may similarly be formed in quartered segments. Notice that the lens material 43 does not block the fan grate 22, and thus there is a hole in the lens material to allow for air flow into the light box 12 as promoted by operation of the fan 20. Note that the fan grate 22 need not be connected to the diffuser 40. In another example, the fan grate 22 can be connected to the fan 20 or to other structures in the light box 12, with the fan grate 22 then positioned in the hole in the diffuser 40 during construction.

FIGS. 3A and 3B also show details of the back plane 50. The back plane 50 is preferably formed of a single sheet of a metallic material such as steel or aluminum. The back plane 50 preferably includes a landing 58 to which the motor 44 of the fan 20 can be mounted. As best seen in FIG. 3B, the landing 58 is connected to the bulk of the back plane 50 via straps 59, thus defining holes 56 around the periphery of the landing 58. These holes 56 allow air flow to pass from the light box 12 into the UV sterilization box 14, as described subsequently. Port 89 in the back plane 50 allows for system signaling to be passed from the UV sterilization box 14 to the electronics on circuit board(s) 24 and to the fan 20, as discussed later.

As noted, the circuit board 24 can be formed in segments, and FIG. 3B shows one such segment. Notice that the circuit board segment 24 includes a cut out 25, which defines a hole when all circuit board segments are positioned in place in the fixture 10. Again, this hole 25 allows for air flow produced by the fan 20. Although such details aren't shown, the circuit board(s) 24 are preferably affixed to the back plane 50, and this can occur in different ways. The circuit board(s) 24 can be screwed to the back plane 50, possibly using stand offs which provide an air gap between the circuit board(s) 24 and the back plane 50. Alternatively, and to promote heat conduction away from the circuit board(s) 24, the circuit board(s) 24 can be affixed in good thermal contact with the back plane 50 using heat conductive tape, paste, or epoxy for example. Although not shows, the outside of the back plane 50 can include heat sinks, as explained in the above-incorporated '900 patent. Note that a benefit of incorporating fan 20 into the light box section 12 is that it promotes heat transfer away from the circuit board(s) 24, as well as air sterilization functionality.

To summarize, when the fan 20 is operating, air is drawn through fan grate 22, through the hole 25 in the circuit board(s) 24, and through holes 56 in the back plane 50 and into the UV sterilization box 14, whose construction is discussed next. As best shown in FIG. 3A, the UV sterilization box 14 includes a bottom surface 60, side surfaces 64, and a top cover 62. The inside of the UV sterilization box 14 includes baffles 70 which direct the air flow in a non-linear path and ultimately to holes 66 formed in the side surfaces 64. As noted earlier, hose connectors 16a and 16b are connected to these holes 66. As will be explained in further detail later, these baffles 70 include UV LED chips 82 to irradiate the air flow as it follows this non-linear path, which is described subsequently with respect to FIG. 4. The baffles 70 preferably comprise a metallic material, and are preferably affixed to the bottom surface 60. For example, the bottom edges of the baffles 70 can be bent 72 and affixed to the bottom surface 60 by spot welding, the use or screws, or the use of adhesives. The side surfaces 64 may be similarly attached to the bottom surface 60. In another example not shown, the baffles 70 may be integrated as a single piece, which can then be dropped into the UV sterilization box 14 during its assembly and affixed in place as necessary.

Components of the fixture 10 may be coated with antimicrobial or reflective materials. For example, the interior surfaces of the UV sterilization box 14 may be coated with Titanium Dioxide. As well as having antimicrobial properties, Titanium Dioxide is highly reflective, thus encouraging reflection of the UV radiation within the UV sterilization box 14. This is preferred to absorption of the UV radiation, because absorption removes useful energy that could otherwise be used for disinfection of pathogens. In one example, the coating can comprise Paint Shield®, manufactured by Sherwin Williams. Such a coating can be applied to the vertical surfaces of the baffles 70, and could also be applied to the underside of the top cover 62, and the top side of the bottom surface 60.

The top cover 62 is preferably affixed to the side surfaces 64 using screws 18. This allows the top cover 62 to be removed to perform maintenance on the fixture 10, such as to clean or remove the baffles 70 or to repair or replace system electronics, as explained subsequently. The top cover 62 can be affixed to the UV sterilization box 14 using other methods which allow it to be opened and reclosed for maintenance purposes. Although not shown, the hose connectors 16a and 16b may also connect to one or more holes provided in the top cover 62.

The UV sterilization box 14 preferably includes a safety switch 103 designed to cut power to the UV LED chips 82 when the top cover 26 is removed. This is to prevent accidental UV exposure to persons who may be assembling or maintaining the light fixture 10. This switch 103 can be provided in the UV sterilization box 14 in different ways, but as shown the switch is mounted to the top flange of the side surface 64. As one skilled will understand, switch 103 includes a contact surface that will be depressed by the top cover 62 when it is connected to the UV sterilization box 14, thus closing the switch 103 and enabling the UV LED chips 82 to receive power. When the top cover 62 is removed, the contact surface is not depressed and switch 103 is thus opened to prevent activation of the UV LED chips 82. Operation of the safety switch 103 is discussed further below with reference to FIG. 5.

The UV sterilization box 14 is preferably fully constructed and then affixed to the light box 12. In the example shown, this occurs using screws 52 which affix the bottom surface 60 of the UV sterilization box 14 to the back plane 50 of the light box 12. However, the UV sterilization box 14 and light box 12 can be affixed using different means. Furthermore, the UV sterilization box 14 and light box 12 need not be separately constructed and then attached to each other. Instead, the fixture 10 may be constructed in a manner that integrates the functionality of the UV sterilization box 14 and the light box 12. Having said this, it can be preferable to manufacture each separately, as this makes it easier to retrofit otherwise standard light boxes 12 with a UV sterilization box 14.

Figure 4:
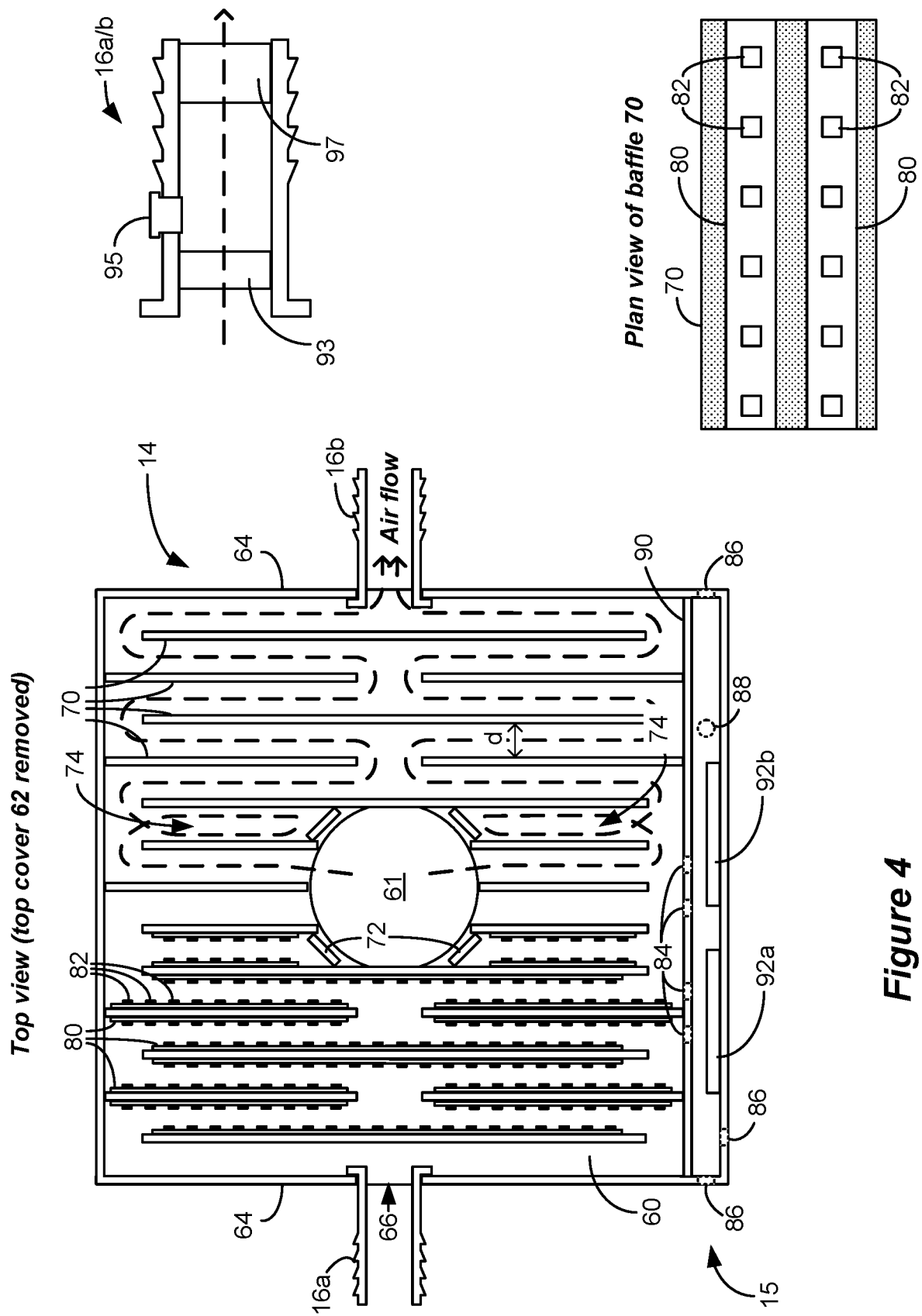
FIG. 4 shows a top down view of the UV sterilization box with its cover removed, including UV LED chips and baffles to define a non-linear path for the air drawn into the fixture by the fan.

As best seen in FIGS. 3A and 4, the bottom surface 60 of the UV sterilization box 14 has a hole 61 of preferably the same diameter as the hole(s) 56 formed in the back plane 50 of the light box 12, which promotes air flow from the fan 20 into the UV sterilization box 14. Once such air enters the UV sterilization box 14, it is directed through a non-linear path as directed by the positioning of the baffles 70. This is best shown in FIG. 4, which shows a top down view of the UV sterilization box 14 with the top cover 60 removed. As shown, the baffles 70 are positioned such that the air flow largely follows a serpentine path from the hole 61 in the bottom surface 60 to the holes 66 in the side surfaces 64 that meet with the hose connectors 16a and 16b. The particular manner in which the baffles 70 are positioned in FIG. 4 splits the air flow into four paths. Two of these air flow paths are shown to the right in FIG. 4, although it should be understood that two other air flow paths would be present in the left of FIG. 4, although these aren't shown for simplicity. Note that the air flow paths may not follow a strict serpentine path. For example, the baffles 70 can be positioned to create vortices 74 in the air flow paths. This effectively elongates the air flow path, which exposes air to UV radiation for a longer time, as explained further below. Baffles 72 can be positioned so as to close the air flow paths as necessary to form vortices 74, as well as to direct the air flow into the baffle structure. Note that the two air flow paths shown to the right eventually join at hole 66 to which hose connector 16b is affixed. The other two air flow paths on the left join at hole 66 to which hose connector 16a is affixed.

To more completely sterilize the air in the air flow paths, the non-linear air flow path includes UV LED chips 82, which may be formed on LED strips 80. The UV LED chips 82 and strips 80 are shown to the left in FIG. 4, although it should be understood that UV LED chips 82 and strips 80 would also be present in the right of FIG. 4, although this isn't shown for simplicity. In the example shown, the LED strips 80 are affixed to the vertical surfaces of the baffles 70, as shown in the plan view at the bottom right in FIG. 4. In this example, there are two UV LED strips 80 spaced vertically on the walls of the baffles 70, which improves exposure of the air to UV radiation.

Preferably, as much of the non-linear air flow paths are exposed to UV radiation as possible, and so in FIG. 4 the UV LED strips 80 are essentially positioned along the entirety of the lengths of the air flow paths, and further preferably are positioned along at least half of these lengths. The width d of the air flow paths around the baffles 70 can may be approximately 1 to 1.5 inches. Assuming that the UV sterilization box 14 is approximately 1.5×1.5 feet (X2, FIG. 1), the length of each of the four air flow paths is approximately 60 to 100 inches, and thus irradiation preferably occurs for at least approximately 30 to 50 inches along these paths. Because the UV radiation may be harmful to people, it is preferable that the UV LED strips 80 not appear in positions where the UV radiation could shine or leak out of the UV sterilization box 14. Thus, for example, the UV LED strips 80 are not proximate the air input hole 61, nor are they proximate the output holes 66 to which the hose connectors 16a and 16b are affixed. UV LED strips 80 may as shown be placed on both sides of the baffles 70, which irradiates the air flow paths from opposing sides. While it is preferred to place the UV LED strips 80 on the vertical surfaces of the baffles 70, they could be placed elsewhere as well, such as on the top side of the bottom surface 60, or the underside of the top cover 62.

Assuming that the height of the UV sterilization box 14 is about 4.5 inches (H2, FIG. 1), the total volume of each of the four air flow paths is approximately 360 cubic inches. Fan 20 may for example comprise Part No. 09225VA-12K-AA-cc, manufactured by NMB Technologies Corp., which moves air with a flow rate of 54 cubic feet/minute, which would move air through each of the four air flow paths in parallel at a flow rate of 13.5 cubic feet/minute, or 389 cubic inches/second. As such, each unit volume of air in each flow path is constantly UV irradiated for approximately one second (360/389), and with a high flux or energy density because the air is being irradiated almost continuously along the length of each air flow path. Note this is advantageous when compared with other air purification system that use UV radiation to purify air. Typically such systems involve a point UV source which the air to be sterilized rushes passed, meaning that each unit volume of air is only radiated for a short time, which may result in incomplete inactivation of pathogens. By contrast, the air is constantly irradiated in the UV sterilization box 14 along the non-linear paths for an extended period of time, and with a high flux or energy density, thus ensuring more complete disinfection. Of course, the extent to which air is UV irradiated could be varied by changing the flow rate of the fan 20, changing the length or volume of the air flow paths, changing the intensity and number of UV LED chips 82 used, etc.

In one example, each of the UV LED chips 82 on UV LED strips 80 produces UV radiation with a peak wavelength in the range of 200 to 280 nm, which generally corresponds to the range of UV-C wavelengths. More preferably, the UV radiation has a peak wavelength in the range of 240 to 260 nm, or in the range of 260 to 280 nm. UV radiation in this range has been shown to be particularly useful to inactivate viruses by targeting their nucleic acids. See K. Bergmann, "UV-C Irradiation: A New Viral Inactivation Method for Biopharmaceuticals," America Pharmaceutical Review, Vol 17(6) (November 2014).

While FIG. 4 shows four air flow paths each following a non-linear path, and two output holes 66, it should be understood that this is just one example. There could be more or less air flow paths established with the UV sterilization box 14, or more or less holes 66. For example, a single non-linear path could comprise a spiral in which air input via hole 61 spirals around the box 14 at increasing diameters, until the sterilized air eventually exits the box at a single output hole 66.

FIG. 4 shows further options that can be included with the UV sterilization box 14, and in particular with the hose connectors 16a and 16b. As shown in the upper right, the interior diameter of the hose connectors 16a/b includes a one-way valve 93 that only allows sterilized air to pass out of the UV sterilization box 14. The hose connectors 16a/b may also include a pressure relief valve 95 which is designed to vent the sterilized air should it exceed the valve 95's pressure. The interior diameter of the hose connectors 16a/b can also include filters 97, such as charcoal filters, to further filter particulates and pathogens, and to also work as an anti-odorant. The anti-odorant properties of the filter 97 can be particularly useful when the fixture 10 is used in a grow farm setting and when the plants being grown have strong odors (e.g., cannabis). The filters and valves need not necessarily be positioned within the hose connectors 16a/16b, but could comprise discrete components connected to the hose connectors 16a/b outside the box 14. Although not shown, the air flow paths within the UV sterilization box 14 could include filters and valves at various points as well.

As shown in FIG. 4, the UV sterilization box 14 can include an electronics section 15. This section 15 can be walled off from the baffles 70 and the air flow paths by a wall 90. Section 15 can include the driver circuitry 92a for driving drive the white LED chips 28 in the light box 12 and driver circuitry 92b for driving the UV LED chips 82 in the UV sterilization box 14. It is preferable that the driver circuits 92a and 92b be separate because the white LED chips 28 and UV LED chips 82 may have different driving requirements (voltages, currents, power, etc.). Driver circuitries 92a and 92b could also be integrated in another example. Electronics section 15 can include or more ports 86 which receive AC power 100 (FIG. 5) from outside the fixture 10, e.g., from a socket or other power source or line to which the fixture 10 is connected. The section 15 may also include a port 88 in the bottom surface 60 to allow signaling to be output from driver circuitry 92a to the white LED chips 28 in the light box 12. Port 88 can correspond in position to a similar port 89 in the back plane 50 of the light box 12 (see FIG. 3B). Although not shown, one skilled will understand that such signaling will connect to connectors or contacts on one or more of the circuit board(s) 24. AC power for the fan 20 can also pass through the ports 88/89.

Electronics section 15 may also include one or more ports 84 to allow signaling to be output from driver circuitry 92b to the UV LED chips 82 in the UV sterilization box 14 and to the safety switch 103. One skilled will understand that such signaling will connect to each of the UV LED strips 80. In this regard, it can be useful to connect the various UV LED strips 80 within the UV sterilization box in a manner to reduce the amount of signaling and connections required. Although not shown, the bottom surface 60 can include a circuit board to assist in routing signaling to the UV LED strips 80. Preferably, port(s) 84 are optically blocked after the signaling has passed through to prevent UV light from entering electronics section 15. It is preferable to include the system electronics within section 15 so it can be easily accessed. For example, top cover 62 of the UV sterilization box 14 can be removed (using screws 18, FIG. 3A), thus allowing access as necessary to maintain or replace system electronics. System electronics could also be located in the light box 12. The size of electronic section 15 can vary depending on the size of the system electronics that are supported.

Figure 5:
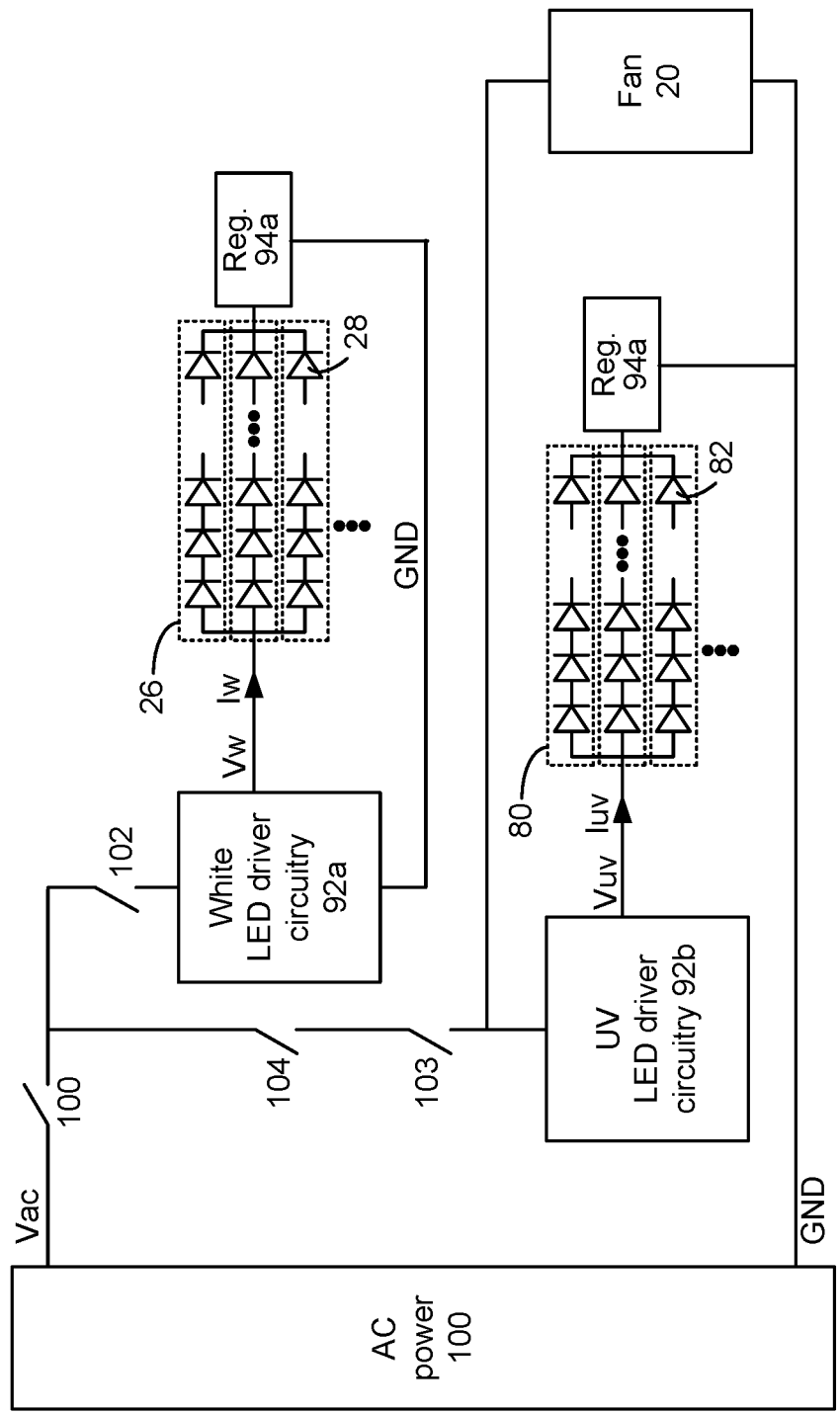
FIG. 5 shows the system electronics for the fixture, including the provision of power to the driver circuitries for the white LED chips, the UV LED chips, and the fan.

System electronics are shown in FIG. 5. AC power provides a voltage Vac, which is provided to the white LED driver circuitry 92a, to the UV LED driver circuitry 92b, and to the fan 20. Although not shown, it should be understood that Vac may be processed (transformed, rectified to DC voltages, etc.) prior to being provided to the driver circuitries 92a and 92b and fan 20 in accordance with their input power needs. White LED driver circuitry 92a typically provides a compliance voltage Vw as necessary to provide a current Iw necessary to drive the white LED chips 28. A regulator 94a can be used to control Iw, as is well known. UV LED driver circuitry 92b is similar, and provides a compliance voltage Vuv as necessary to provide a current Iuv necessary to drive the UV LED chips 82, with a regulator 94b controlling Iuv. In one example, the power required by the fixture 10 may comprise about 100 Watts, with the white LED chips 28 requiring about 60 W, the UV LED chips 82 requiring approximately 30 W, and the fan requiring about 10 W.

It may be desired to separately control one or more aspects of the fixture 10. For example, it may be desired at a given time to drive only the white LED chips 28 to provide illumination to a room the fixture 10 is placed in, but to not drive the UV LED chips 82 to provide UV disinfection. Conversely, it may be desired at a given time (e.g., at night) to drive only the UV LED chips 82 to provide UV disinfection, but to not drive the white LED chips 28 to provide illumination. In this regard, the fixture 10 can include or be controlled by one or more switches 100, 102, or 104. For example, switch 100 comprises a master switch used to control all operations of the fixture, i.e., to control driving the white and UV LED chips 28 and 82, and the fan 20. Switch 102 can be used to independently control the white LED chips 28. Switch 104 can be used to independently control the UV LED chips 82 and the fan 20. Switch 104 is useful because it would normally be expected that the fan 20 and UV LED chips 82 would be enabled together, with the fan 20 drawing air flow into the UV sterilization box 14 that includes the chips 82. That being said, the UV LED chips 82 and fan 20 could also be independently controlled by their own switches. Any of the switches shown could comprise wall-mounted switches to which the fixture 10 is connected. Alternatively, the switches can appear in the light fixture (section 15) as part of the system electronics. In this respect, the switches may be controlled by a remote control, with system electronics including a wireless receiver (e.g., a Bluetooth receiver) for receiving input from the remote control.

System electronics can further include a safety switch 103. As described earlier, this switch 103 is designed to open to cut power to the UV LED chips 82 (e.g., via driver circuitry 92b) when the top cover 62 is removed from the UV sterilization box 14. As shown, safety switch 103 is in series with switch 104, and so would also disable power to the fan 20. However, switch 103 could also be located in the circuitry to cut power to only the LED driver circuitry 92b.

Figure 6A:
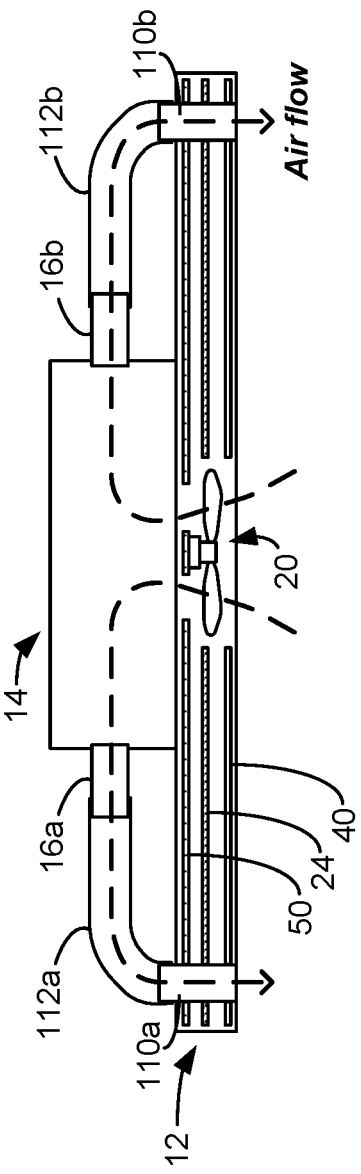
FIG. 6A shows that sterilized air output from the UV sterilization box can be output back into a room through ports provided in the light box.
Figure 6A:
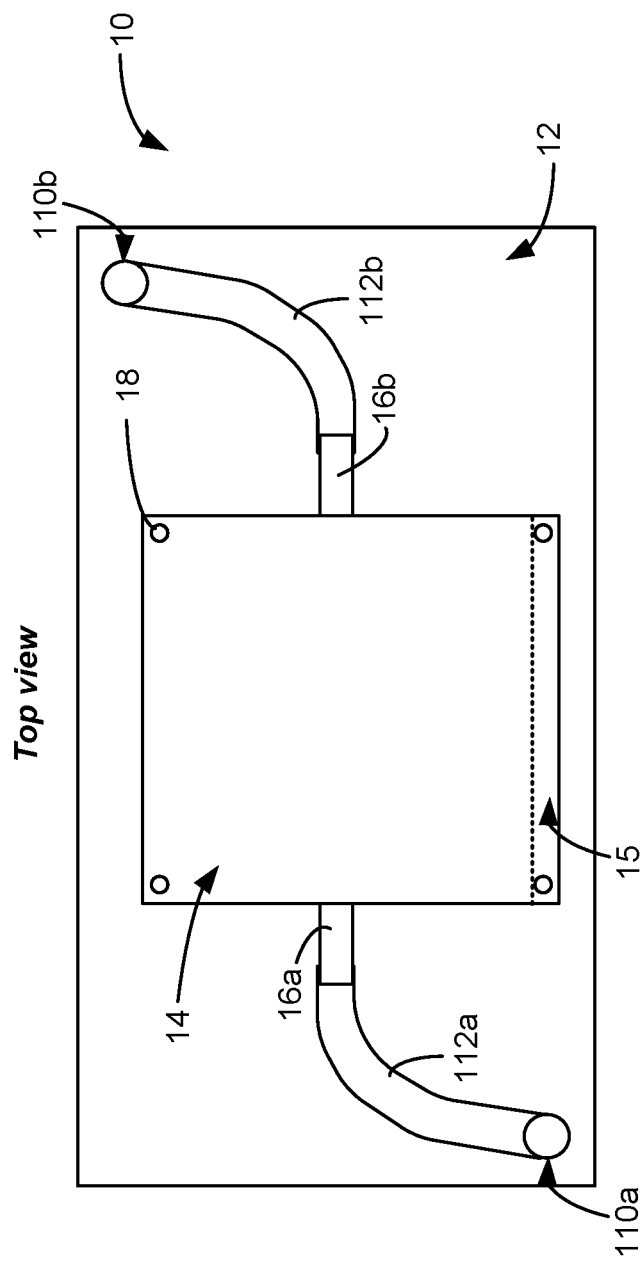
Figure 6B:
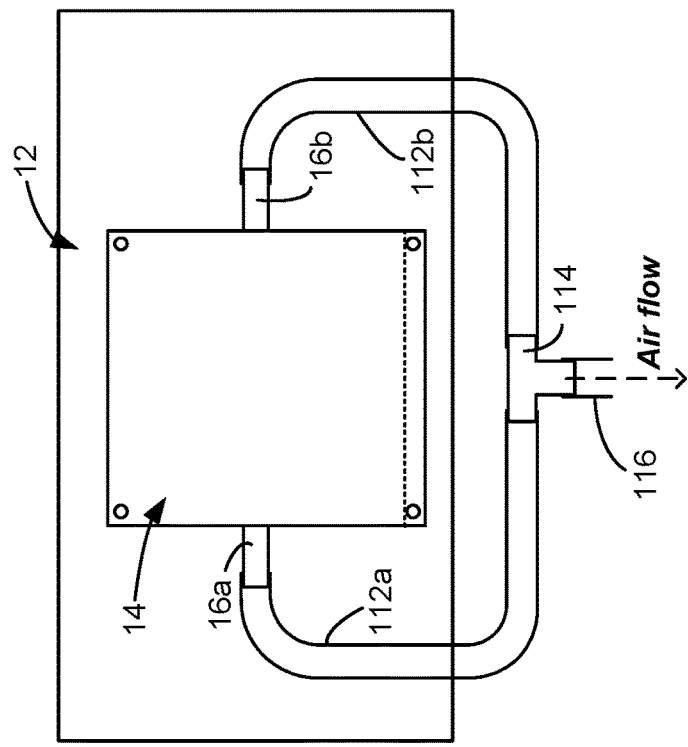
FIG. 6B shows that sterilized air outputs from the UV sterilization box can be combined.
Figure 6C:
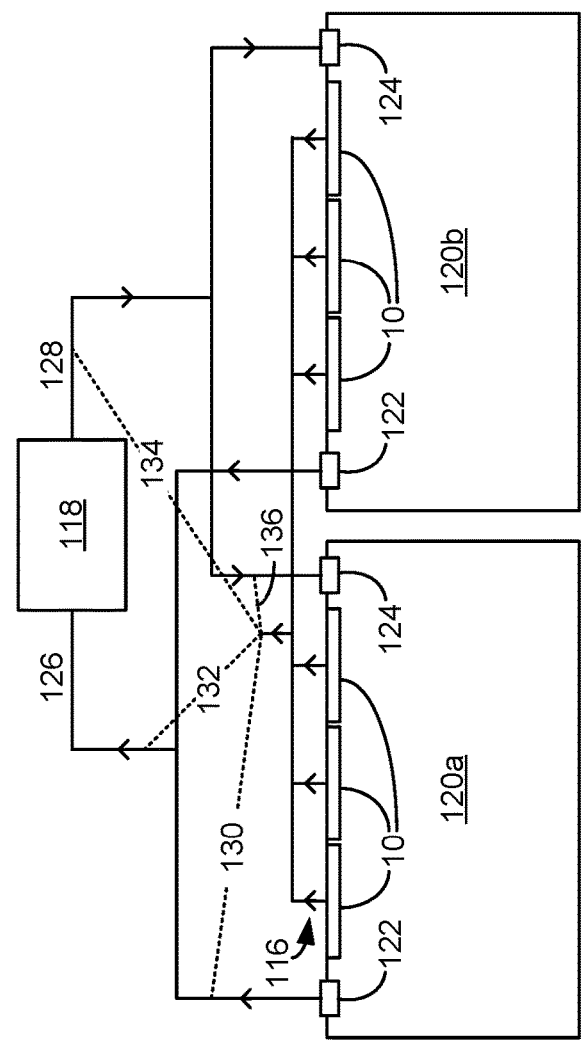
FIG. 6C shows how that sterilized air can be output into the air handling system of a building or house.

As discussed above, the UV sterilization box 14 includes one or more hose connectors 16a and 16b which output sterilized air, and such sterilized air is preferably distributed back into the room or building in which the fixture 10 appears. FIGS. 6A-6C show different examples of how this can occur. Sterilized air can also effectively be disposed with, such as by venting such air into the plenum space in a building or house, or through a vent to the outside environment.

FIG. 6A shows an example in which the sterilized air is output back into the room through the fixture 10 itself. In this example, which shows a larger light fixture (2×4 foot), the light box 12 includes one or more hose ports. Two such ports 110a and 110b are shown in FIG. 6A, and may comprise hose connectors allowing them to be joined to the hose connectors 16a and 16b by hoses 112a and 112b as shown. The ports 110a and 110b in this example proceed through holes in the back plane 50, the circuit board(s) 24, and the diffuser 40 of the fixture 10. Although not shown, the air output from the hose connectors 16a and 16b can be combined (e.g., FIG. 6B) and put back into the room through a single port 110 in the light box 12, or through more than two ports.

FIG. 6C shows that the air output from the hose connectors 16a and 16b can be placed into the air handling system in a building in which one or more fixtures 10 are placed, thus providing sterilized air to one or more rooms in the building. In this example, it is assumed that the building has a number of rooms (two of which 120a and 120b are shown) with each room having a number of fixtures 10 (three in each as shown). The building includes an air handler 118 with an input 126 and an output 128. One skilled will recognize that the duct work of an air handling system could include other components that are not shown, such as fans, exhaust vents, fresh air inputs, etc. Each room 120a and 120b has a supply vent 124 connected to the output 128 and a return vent 122 connected to the input 126. FIG. 6B shows that the air output from the hose connectors 16a and 16b in a given fixture 10 can be combined (e.g., FIG. 6B) using a junction 114, which outputs to an output hose 116. Junction 114 and output hose 116 could also be fit with filters (97) and valves (93, 95), as explained earlier with reference to FIG. 4. The outputs from several output hoses 116 can be connected as shown in FIG. 6C, and connected by another hose or duct work to any convenient point in the air handler duct system, including the return line of a given room (130), the input 126 to the air handler 118 (132), the output of the air handler 118 (134), or to the supply line of a given room (136). In any of these examples, the sterilized air is ultimately provided back into the room(s).

Many modifications to the disclosed fixture 10 can be made, and the fixture 10 can be used in different environments to useful ends. For example, the white LED chips 28 may not include significant peaks at either or both of 405 nm or 470 nm, although the inclusion of these wavelengths is preferred to further aid sterilization that the fixture 10 provides. In fact, the white LED chips 28 may not be used, and instead other white light sources (e.g., bulbs) could be used in the fixture 10, with disinfection occurring strictly through use of the fan 20 and the UV sterilization box 14. The UV sterilization box 14 could include UV radiation sources other than UV LED chips. For example, various UV emitting bulbs could be used inside the UV sterilization box 14.

The fixture 10 can be used in environments where pathogens may be present, and in particular air borne pathogens. This can include hospitals, nursing homes, operating rooms, restrooms, kitchens, etc. Fixture 10 can also be used in a grow farm setting, in which light fixtures 10 are used to grow plants. For example, the disclosed fixture can be used in the context of the above-incorporated '900 patent, and can include the various improvements to a light fixture that are disclosed in that document.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A light fixture, comprising:
    a light box comprising a back plane with an inside surface and an outside surface, and a diffuser parallel with the back plane;
    a plurality of white light sources located in the light box and configured to provide illumination to an environment through the diffuser;
    a fan configured to draw air from the environment into the light box, wherein the fan is located in the light box and wherein the drawn air is output by the light box through the back plane, wherein the fan is mounted to the inside surface of the back plane; and
    a sterilization box connected to the outside surface of the back plane and comprising at least one path configured to receive the drawn air output from the light box and to output sterilized air at one or more openings, wherein the sterilization box comprises a plurality of ultra violet (UV) radiation sources configured to irradiate the drawn air with UV radiation along each at least one path to produce the sterilized air.

2. The light fixture of claim 1, wherein the white light sources comprise light emitting diode (LED) chips.

3. The light fixture of claim 2, wherein a spectrum of the illumination includes a peak with a wavelength at approximately 405 nm.

4. The light fixture of claim 2, wherein a spectrum of the illumination includes a peak with a wavelength at approximately 470 nm.

5. The light fixture of claim 2, wherein each of the plurality of white LED chips includes a plurality of LEDs.

6. The light fixture of claim 5, wherein a first of the plurality of LEDs in each white LED chip is configured to produce radiation with a peak at approximately 405 nm, and wherein a second of the plurality of LEDs in each white LED chip is configured to produce radiation with a peak at approximately 470 nm.

7. The light fixture of claim 1, further comprising a grate for the fan, wherein the fan grate is in contact with the diffuser.

8. The light fixture of claim 1, wherein each at least one path is non-linear.

9. The light fixture of claim 8, wherein each at least one path is serpentine or spiral along at least a portion of its length.

10. The light fixture of claim 8, wherein the at least one air flow path is defined by one or more baffles within the sterilization box.

11. The light fixture of claim 10, wherein the UV radiation sources are affixed to sides of the baffles.

12. The light fixture of claim 1, wherein the UV radiation sources comprise UV LED chips configured to produce the UV radiation with a peak wavelength in the range from 200 to 280 nm.

13. The light fixture of claim 1, wherein the ultra violet (UV) radiation sources are configured to irradiate the drawn air with UV radiation along at least a majority of a length of each at least one path.

14. The light fixture of claim 1, further comprising one or more ports through the light box, wherein the sterilized air is provided from the one or more openings through the one or more ports to output the sterilized air to the environment.

15. The light fixture of claim 1, further comprising at least one filter configured to filter the sterilized air.

16. The light fixture of claim 1, wherein the sterilization box comprises a removable top cover.

17. The light fixture of claim 1, wherein the light box further comprises a frame to hold the back plane and the diffuser.

18. The light fixture of claim 1, further comprising one or more circuit board sections within the light box, wherein the one or more circuit board sections comprise the plurality of white light sources.

19. The light fixture of claim 1, wherein the inside surface of the back plane comprises a landing, wherein the fan comprises a motor, wherein the motor is mounted to the landing.

* * * * *